(12) United States Patent
Ishida

(10) Patent No.: US 6,467,621 B1
(45) Date of Patent: Oct. 22, 2002

(54) PACKAGE OF SHEET-TYPE PATCHES

(75) Inventor: Koichi Ishida, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/331,579

(22) PCT Filed: Oct. 30, 1998

(86) PCT No.: PCT/JP98/04927

§ 371 (c)(1), (2), (4) Date: Aug. 26, 1999

(87) PCT Pub. No.: WO99/23012

PCT Pub. Date: May 14, 1999

(30) Foreign Application Priority Data

Oct. 31, 1997 (JP) .............................................. 9-314600

(51) Int. Cl.[7] .............................................. B65D 73/00
(52) U.S. Cl. ........................ 206/460; 206/440; 206/484
(58) Field of Search ................................ 206/460, 438, 206/440, 441, 484

(56) References Cited

U.S. PATENT DOCUMENTS

| | | | | |
|---|---|---|---|---|
| 3,070,102 A | * | 12/1962 | MacDonald | 206/460 |
| 3,283,888 A | * | 11/1966 | Scott | 206/460 |
| 3,416,525 A | * | 12/1968 | Yeremian | 206/440 |
| 3,985,383 A | * | 10/1976 | Yonkers | 206/460 |
| 4,022,203 A | * | 5/1977 | Ackley | 128/156 |
| 4,557,381 A | * | 12/1985 | Whitney | 206/440 |
| 4,666,040 A | * | 5/1987 | Murata | 206/441 |
| 4,881,359 A | * | 11/1989 | Schirmer | 53/427 |
| 5,566,826 A | * | 10/1996 | Evans | 206/409 |
| 5,628,724 A | * | 5/1997 | DeBusk et al. | 602/58 |
| 5,910,125 A | * | 6/1999 | Cummings et al. | 602/58 |

* cited by examiner

Primary Examiner—Shian Luong
(74) Attorney, Agent, or Firm—Oblon, Spivak, McClelland, Maier & Neustadt, P.C.

(57) ABSTRACT

The present invention relates to a package of sheet-type patches (1) which are applied to the face, and to a method for producing the same. In the invention, sheet-type patches (1) each comprising a pack agent layer (13) formed on a substrate (12) and covered with a liner layer (14) are packaged in a package pouch (19) in which said sheet-type patches (1) are fixed onto the inner surface of the package pouch (19) via their liner layer (14). The sheet-type patches (1) can be fixed onto the inner surface of the package pouch (19) by means of an adhesive or electrostatic force. According to the invention, the process of producing sheet-type patches (1) and packaging them is much simplified, and the production efficiency in the process is much improved. In the package of sheet-type patches (1) of the invention, the patches do neither move nor adhere to each other.

5 Claims, 5 Drawing Sheets

PACKAGE OF SHEET-TYPE PATCHES

FIELD OF THE INVENTION

The present invention relates to a package of sheet-type patches which are applied to the face, and to a method for producing the same.

BACKGROUND OF THE INVENTION

Various sheet-type patches have heretofore been proposed, which are applied to the face portion, for example, under the eyes. Those sheet-type patches are produced by forming a pack agent layer on an appropriate substrate, for example, of non-woven fabric, followed by covering the layer with a liner or support.

For packaging those sheet-type patches, employed is a method of completely cutting a sheet comprising a pack agent layer formed on a substrate and covered with a liner or support into individual patches, followed by packaging the resulting individual patches in package pouches. Alternatively, also employed is another method of half-cutting the same sheet to form patches as supported on the liner or support that is not cut (see FIG. 2).

However, where the sheet-type patches are completely cut out along with the liner or support into individual ones and the individual patches are packaged in package pouches, the packaged sheet-type patches will move in the package pouches. In particular, where a plurality of patches are packaged in one package pouch, there occurs a problem that the patches adhere to each other in the pouch.

On the other hand, where the sheet is half-cut to form patches as supported on the liner or support that is not cut, the substrate and the pack agent layer cut off from the sheet shall be wasted. In addition, in this case, the size of the package pouches to be used must be large. Moreover, the working conditions for half-cutting the preformed sheet must be strictly controlled. In particular, where the pack agent in the preformed sheet contains a water-soluble polymer compound as crosslinked with a polyvalent metal, it is difficult to half-cut the sheet into separate patches and to trim the patches, if the crosslinking in the pack agent layer is not fully completed. For these reasons, the half-cutting and packaging method is problematic in that the production efficiency is very poor and that the size of the package pouches to be used must be large. In addition, where a silicone-processed, peelable film are used as the liner for the patches, there also occurs a problem that the pack agent layer itself will be peeled off while trimming, and that, after packaged, the patches will move in the package pouches.

The object of the present invention is to improve the production efficiency in the process of producing sheet-type patches and packaging them, thereby making good use of raw materials for packaged sheet-type patches. Another object of the invention is to provide packaged sheet-type patches which do neither move nor adhere to each other in the package pouches, and to provide a method for producing them.

SUMMARY OF THE INVENTION

In the invention, sheet-type patches each comprising a pack agent layer formed on a substrate and covered with a liner layer are packaged in a package pouch while they are fixed onto the inner surface of the package pouch via the liner layer.

The package of sheet-type patches of the invention can be produced, for example, by fixing sheet-type patches, which are prepared by forming a pack agent layer on a substrate, covering it with a liner layer, and thereafter cutting the thus-coated substrate into separate patches having a desired shape, onto the inner surface of a packaging film via the liner layer of each patch, by means of an adhesive or electrostatic force, followed by sealing the film to produce a package pouch.

Specifically, in the invention, a sheet having a structure of substrate/pack agent layer/liner layer is completely cut into individual patches having a desired shape, and the resulting patches are directly fixed onto the inner surface of a package pouch, whereby the patches are integrated with the package pouch.

According to the present invention, the process of producing sheet-type patches and packaging them is much simplified, and the production efficiency in the process is much improved. In addition, the raw materials for the patches are not wasted. Moreover, in the package of sheet-type patches of the invention, the patches do neither move nor adhere to each other.

BRIEF DESCRIPTION OF THE DRAWINGS

In FIG. 1, (a) is a partly-cut perspective view of the package, and (b) is a cross-sectional view of (a) as cut along the line A—A.

In FIG. 2, (a) is a partly-cut perspective view of the package, and (b) is a cross-sectional view of (a) as cut along the line B—B.

In FIG. 3, (a) is a plan view of the package; (b) is a cross-sectional view of (a) as cut along the line C—C; and (c) is a side view showing the condition of a sheet-type patch fixed onto a packaging film.

DETAILED DESCRIPTION OF THE PREFERRED EMBODIMENT

Figure 1:
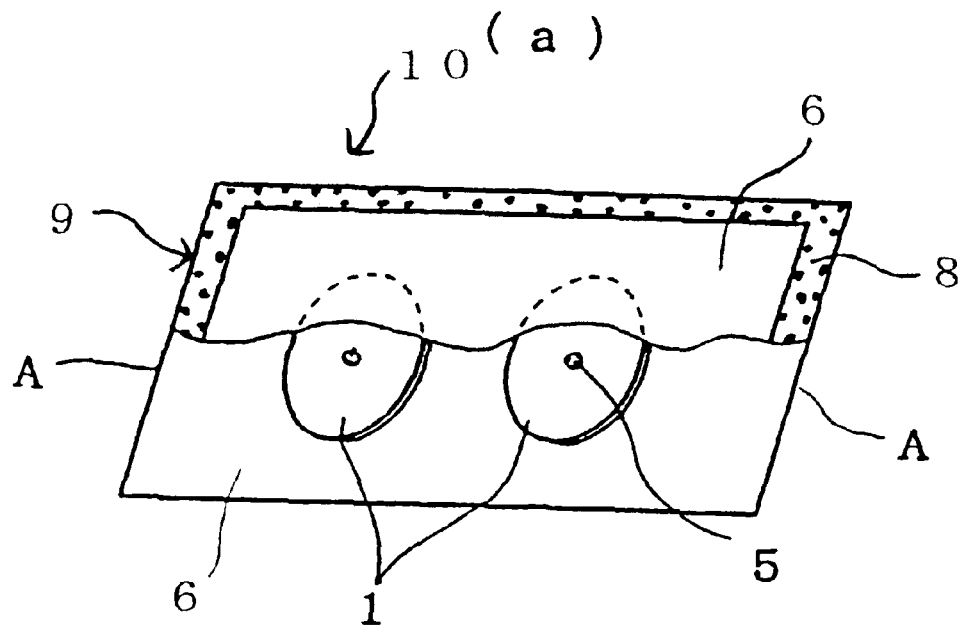
FIG. 1 shows one embodiment of the package of sheet-type patches of the invention.
Figure 1:
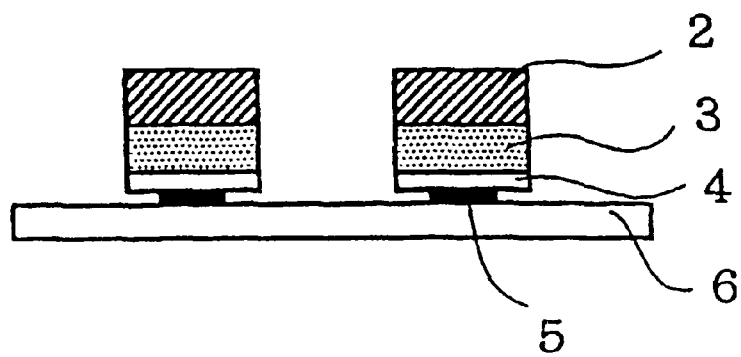

The material for the substrate for the sheet-type patches of the invention is not specifically limited. Any material usable for producing ordinary sheet-type patches is employable herein, including, for example, knitted or woven fabrics of flannel, staple fiber muslin; various non-woven fabrics; paper, plastics, etc.

The pack agent composition to be applied on the substrate by dipping or coating is not also specifically limited, and may be any ordinary one. It comprises, for example, any of moisturizers such as glycerin, sorbitol, polyethylene glycol; various cosmetically-active ingredients such as keratinization retardants, wrinkling retardants, whitening agents; other pharmaceutical ingredients; water-soluble polymer compounds crosslinked with poly-valent metals and containing water, oily components and others; film-forming compounds such as polyvinyl alcohol, polyvinyl pyrrolidone, polyvinyl acetate emulsion, carboxymethyl cellulose, along with a vehicle of an inorganic powder of kaolin, talc, bentonite, titanium dioxide, zinc oxide and the like.

The water-soluble polymer compounds usable in the pack agent composition in the invention are not specifically limited, but preferred are poly(meth)acrylic acids. The poly (meth)acrylic acids referred to herein are meant to include homopolymers and copolymers of (meth)acrylic acid, homopolymers and copolymers of (meth)acrylates, copolymers of (meth)acrylic acid and (meth)acrylates, their partially-neutralized products, and their mixtures. The (meth)acrylic acid means acrylic acid and methacrylic acid. The type of the salts for poly(meth)acrylates is not specifically limited, but generally used are sodium salts. Preferably, those water-soluble polymer compounds are in the composition in an amount of from 1 to 30% by weight, more preferably from 2 to 15% by weight of the total composition. Also preferably, the water-soluble polymer compounds are used in the form of their crosslinked products, especially those with poly-valent metals.

Water-soluble salts are preferred as the poly-valent metal salts used as the crosslinking agents for the water-soluble polymer compounds, which include, for example, calcium chloride, magnesium chloride, aluminium chloride, potash alum, ammonium alum, iron alum, aluminum sulfate, ferric sulfate, magnesium sulfate and the like.

The amount of the crosslinking agent to be used may be generally from 0.01 to 5 equivalents, but preferably from 0.1 to 2 equivalents, relative to one equivalent of the crosslinkable site of the water-soluble polymer compound. If the amount of the poly-valent metal salt used is smaller than 0.05 equivalents, it will be sequestered and could not act to gel the polymer. On the other hand, if the amount is larger than 5 equivalents, the degree of crosslinking of the polymer will be too high, thereby causing separation of water from the crosslinked polymer.

As the active ingredient, one or more of methyl salicylate, indomethacin, 1-menthol and the like that are generally used in the art may be formulated in the composition. For skin-care purposes, any of various cosmetically-active substances, moisturizers, animal and vegetable extracts, vitamins and the like that are used in conventional cosmetics may also be formulated in the composition. Preferably, the amount of the active ingredient is from 0.01 to 20% by weight of the total composition.

As preferred examples of the oily component to be in the composition, mentioned are primary alcohol-fatty acid esters of the following general formula:

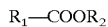

wherein $R_1$ represents a linear or branched alkyl group having from 2 to 18 carbon atoms; and $R_2$ represents a linear or branched alkyl group having from 1 to 18 carbon atoms. Of those, especially preferred are isopropyl myristate and octyldodecyl myristate, as they have good capabilities of improving the releasability and endermic absorbability of active ingredients, and they irritate little the skin. The amount of the oily component is preferably from 1 to 20% by weight, more preferably from 2.5 to 10% by weight of the total composition.

Since the water content of the pack agent composition is high, silica is preferably used as an oil-gelling agent in the composition. As the silica, preferred is anhydrous light silica, especially that having a mean grain size of primary grains of from 1 to 500 mμ, more preferably from 5 to 100 mμ. The oil-gelling agent stabilizes uniform dispersion of oily components in the pack agent composition, while preventing the oily components from bleeding out. Containing the oil-gelling agent, therefore, the composition gives no sticky feel to the skin and is comfortable. Preferably, the amount of the oil-gelling agent to be added is from 1 to 15% by weight, more preferably from 2 to 10% by weight of the total composition.

Apart from the components mentioned above, the pack agent composition of the invention may optionally contain one or more moisturizers generally used in ordinary pack agents, in an amount of from 5 to 40% by weight of the total composition. In addition, the composition may further contain one or more inorganic powders of kaolin, talk and the like, in an amount of from 0 to 30% by weight of the total composition. Further, in order to modulate the physical properties (flexibility, stickiness, shape retentiveness, etc.) of the plaster-like composition, any suitable polymer compounds such as polybutene, acrylic resin emulsion and the like may be added to the composition.

The pack agent composition for use in the invention may contain water generally in an amount of not smaller than 30% by weight, but preferably from 40 to 80% by weight.

In the invention, the pack agent composition is applied onto a substrate such as non-woven fabric or the like by dipping or coating to form a pack agent layer thereon, and the pack agent layer is covered with a liner layer to prepare a long sheet for patches. Next, the long sheet is completely cut into patches having a desired shape, and the resulting sheet-type patches are fixed onto a packaging film. Next, the packaging film is sealed into pouches. In that manner, the patches are integrated with the package pouches.

The packaging film for use in the invention is not specifically limited, but, in general, used are plastic films.

Plastic materials suitable for forming the plastic films may be thermoplastic resins, which include, for example, polyolefins such as crystalline polypropylene, crystalline propylene-ethylene copolymers, crystalline polybutene-1, crystalline poly-4-methylpentene-1, low-, middle- or high-density polyethylenes, ethylene-vinyl acetate copolymers (EVA), ethylene-ethyl acrylate copolymers (EEA), ion-crosslinked olefin copolymers (ionomers); aromatic vinyl polymers such as polystyrene, styrene-butadiene copolymers; halogenovinyl polymers such as polyvinyl chloride, vinylidene chloride resins; nitrile polymers such as acrylonitrile-styrene copolymers, acrylonitrile-styrene-butadiene copolymers; polyamides such as nylon-6, nylon-66, para- or meta-xylylene adipamide; polyesters such as polyethylene terephthalate, polytetramethylene terephthalate; various polycarbonates; polyacetals such as polyoxymethylene.

Films of those plastic materials may be non-oriented ones, or may be monoaxially or biaxially oriented for use in the invention.

The plastic films which are used as packaging films in the invention may be single-layered ones or may be multi-layered laminates composed of two or more of those films. If desired, one or more of those plastic films may be laminated with metal foil of aluminium or the like, and/or with paper, cellophane or the like.

Preferred are multi-layered laminate films of the plastic films that comprise an interlayer of aluminium foil(Al). As embodiments of the layer constitution of the laminate films, mentioned are 1) polyethylene terephthalate (PET)/Al/ ionomer resin/copolypropylene (CPP); 2) PET/Al/low-density polyethylene (LDPE)/CPP; 3) PET/Al/linear low-density polyethylene(L-LDPE)/CPP; 4) nylon(Ny)/Al/ ionomer resin/CPP; 5) Ny/Al/LDPE/CPP; 6) Ny/Al/L-LDPE/CPP, etc.

As one embodiment of fixing sheet-type patches onto the packaging film, mentioned is a method of using an adhesive for the fixation. One preferred mode of this embodiment comprises the steps mentioned below.

1) An adhesive is partly applied to a packaging film in the area to which sheet-type patches are fixed, and sheet-type patches as cut to have a desired shape are fixed onto the film at the adhesive-coated position, via the liner layer of each patch.

2) Next, the packaging film is sealed to form a package pouch in which the patches are integrated with the package pouch.

For fixing the patches onto the packaging film, it is desirable that an adhesive is partly applied to the packaging film around the center of the part at which each sheet-type patch is fixed (see FIG. 1). The adhesive may be spotwise or spirally applied to the desired position of the film at which each sheet-type patch is fixed, or may be applied thereto by spraying. Alternatively, an adhesive may be applied to the liner layer of each sheet-type patch as cut to have a desired shape, and the patch may be fixed onto the packaging film. The adhesive to be used for the fixation of the sheet-type patches is not specifically defined, but preferred are hot-melt adhesives, such as olefinic adhesives, rubber adhesives and the like.

In another embodiment of fixing sheet-type patches onto the packaging film, employed is electrostatic force. One preferred mode of this embodiment comprises the steps mentioned below.

1) At least one of the liner layer of each sheet-type patch and the packaging film is electrostatically charged.

2) The sheet-type patch as cut to have a desired shape is fixed onto the packaging film by means of electrostatic force.

3) Next, the packaging film is sealed to form a package pouch in which the patches are integrated with the package pouch.

In this case, the liner layer of each sheet-type patch and the layer of the packaging film to be the inner surface of the package pouch must be made of dielectrics. For this, at least one of the liner layer and the packaging film shall be electrostatically chargeable. The liner layer of the sheet-type patch may be electrostatically charged, while it is still in the non-cut long sheet to be cut into patches. It may also be charged, after the patches are cut out of the long sheet to have a desired shape.

In the method of fixing the sheet-type patches onto the packaging film by means of electrostatic force, the liner layer of the patch and/or the packaging film may be entirely and uniformly charged. Therefore, the working efficiency in the method is good. In particular, the method is advantageous when a large number of sheet-type patches are packaged in one package pouch. In addition, in the packages formed in this method, not only the sheet-type patches are fixed onto the packaging film by electrostatic force, but also the upper-side and lower-side film to form the package pouch are attracted to each other by electrostatic force. Therefore, in the method, sealing the film into the package pouch does not require any external force to degas the pouch. Accordingly, in the method, it is possible to easily degas the package, without crushing the delicate sheet-type patches therein, to thereby reduce the bulk of the package.

The package of sheet-type patches of the invention can be produced by overlaying another packaging film on the packaging film, which has sheet-type patches as fixed thereon, to form a package pouch, followed by heat-sealing the edges of the films. Alternatively, one packaging film which has sheet-type patches as fixed thereon may be folded to form an envelope, and the open edges of the envelope may be heat-sealed into a package pouch.

Figure 5:
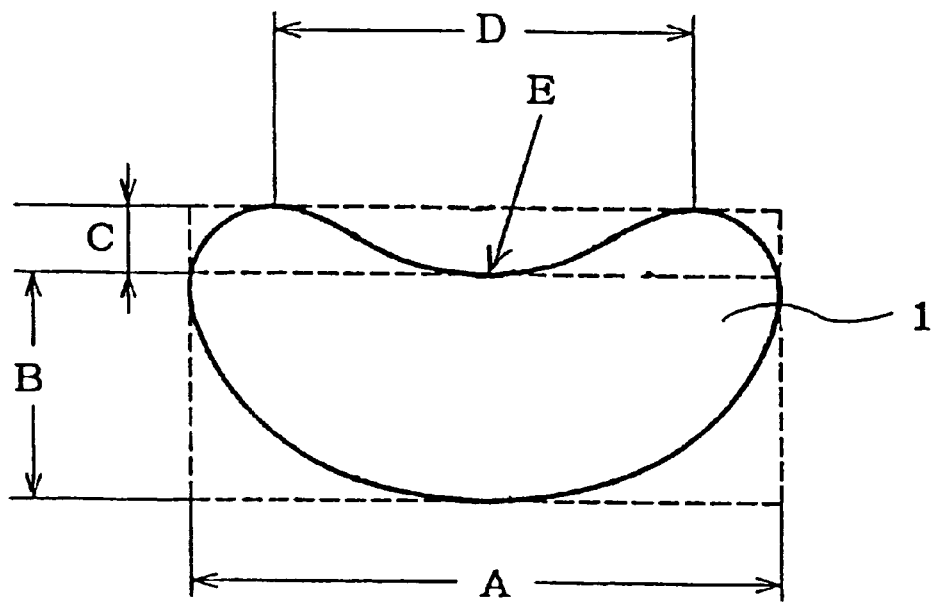
FIG. 5 is a plan view showing one example of a sheet-type patch.

The sheet-type patches to be packaged herein may be prepared by cutting a long sheet for the patches in any desired shape. For example, for skin-care use for treating the areas outside and under the eyes, the patches preferably have the shape as illustrated in FIG. 5.

Figure 6:
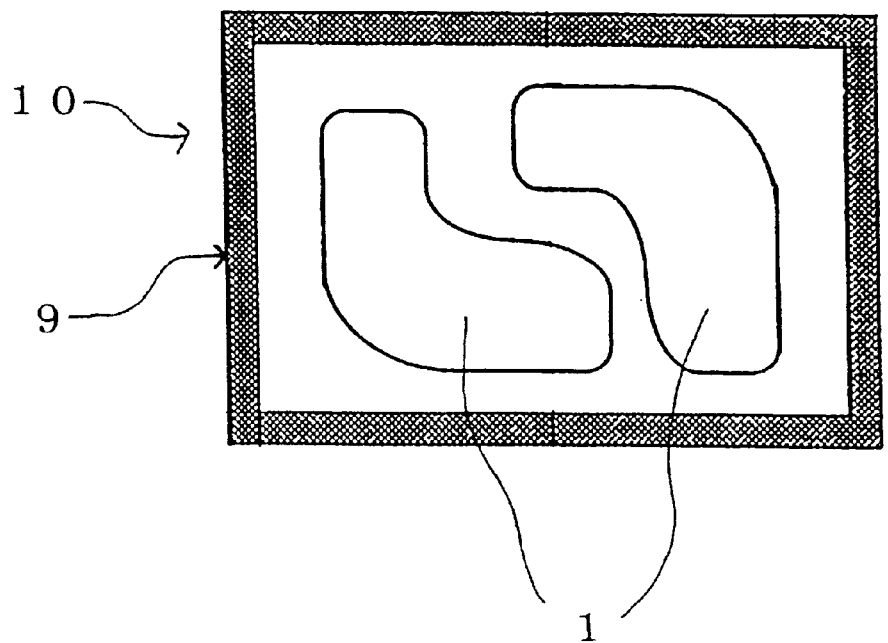
FIG. 6 is a plan view showing another example of a sheet-type patch.

For the package of a pair of bilaterally symmetric patches, which are for the areas outside and under the eyes and for the areas around the nasolabial grooves, it is desirable that the pair of bilaterally symmetric patches are fixed onto the inner surface of the packaging film in such a manner that they face to each other (see FIG. 6). Where the pair of such patches are positioned in that manner, the space for the patches may be reduced. If desired, a large number of such patches may be packaged in one package pouch.

Now, the package of sheet-type patches of the invention is described in more detail hereinunder with reference to the drawings attached hereto. The examples are given solely for the purpose of illustration, and are not to be construed as limitations of the present invention, since many variations thereof are possible without departing from its spirit and scope.

EXAMPLE 1

FIG. 1 shows one embodiment of the package of sheet-type patches of the invention, in which the numeral reference 1 is a sheet-type patch, 5 is an adhesive, 6 is a packaging film, 9 is a package pouch, and 10 is a package of sheet-type patches.

In this embodiment, the patch 1 is composed of a non-woven fabric substrate 2, a pack agent layer 3 and a liner layer 4, and its center is directly fixed onto the packaging film 6 with the hot-melt adhesive 5 via its liner layer 4. Another packaging film 6 is laid over the thus-fixed patches 1, and the edges 8 of the resulting package pouch 9 are sealed to form the package 10.

Figure 2:
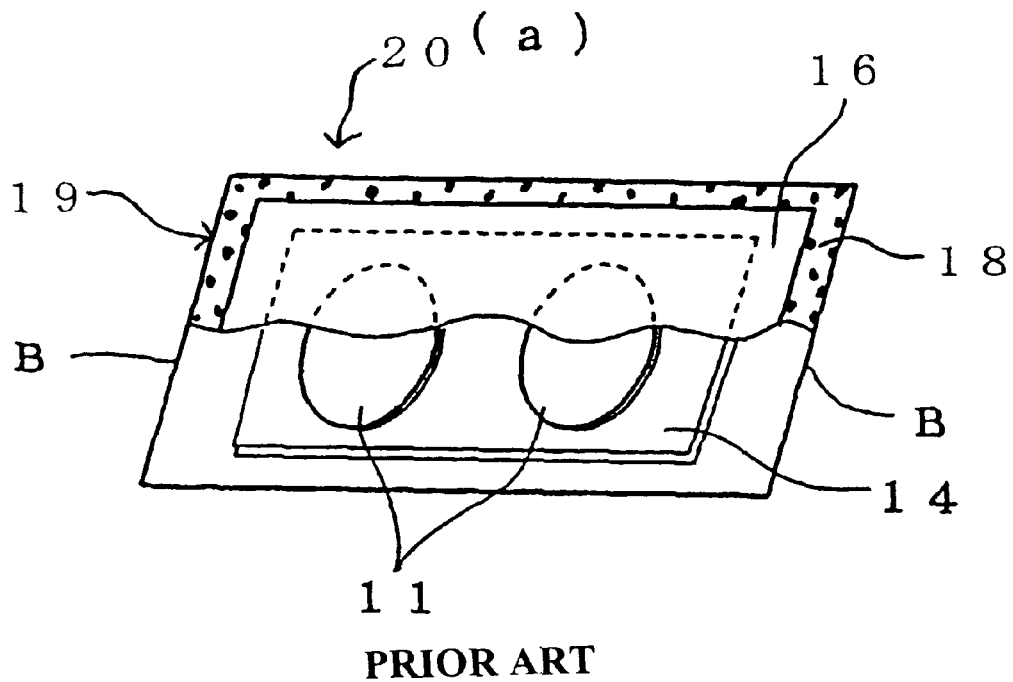
FIG. 2 shows one example of a conventional package of sheet-type patches.
Figure 2:
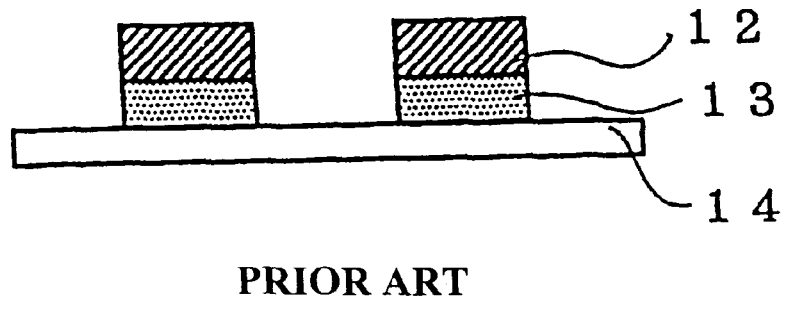

As opposed to this, in the prior art technique as illustrated in FIG. 2, the sheet-type patches 11 are prepared by half-cutting a long sheet composed of a substrate 12, a pack agent layer 13 and a liner layer 14. In this case, the liner layer 14 is not cut at all, but shall act as the support in the package of the patches. The pair of half-cut patches 11 are inserted into the package pouch 19 along with the support 14, and the edges 18 of the pouch 19 are sealed to form the package 20 containing the patches 11 therein.

In the package 10 in FIG. 1, the patches 1 are integrated with the package pouch 9, and therefore do neither move nor adhere to each other.

However, in the package 20 in FIG. 2, the substrate and the pack agent not used in the separated patches 11 shall be wasted. In addition, in this case, the step of half-cutting the long sheet requires strictly controlled working conditions. In particular, where the pack agent in the long sheet contains a water-soluble polymer compound as crosslinked with a polyvalent metal, cutting and trimming the patches 11 out of the long sheet could be effected only after the crosslinking in the pack agent layer 13 is fully completed. Therefore, prior to the step of cutting the patches out of the long sheet, the pack agent layer must be fully crosslinked and aged for a long period of time, and, in addition, the cutting step must be followed by the additional step of inserting the patches into the package pouch 19.

Different from the prior art method, the method of the invention for producing the package 10 of FIG. 1 does not require any strict working conditions for cutting the patches, since, in the method, the long sheet for the patches 1, having the structure of substrate 2/pack agent layer 3/liner layer 4, may be completely cut into the patches 1. Even if the pack agent contains a water-soluble polymer compound as crosslinked with a polyvalent metal, the long sheet may be efficiently and easily cut into the patches 1 before the crosslinking of the compound is not as yet completed. Accordingly, for producing the package of sheet-type patches of the invention, the steps of forming the long sheet for patches, cutting the long sheet into individual patches, fixing the patches onto a packaging film, and sealing the film into a package pouch can be continuously effected in one continuous process, therefore, the production efficiency in the continuous process is extremely high. In addition, the raw materials for the patches 1 are not wasted.

EXAMPLE 2

Figure 3:
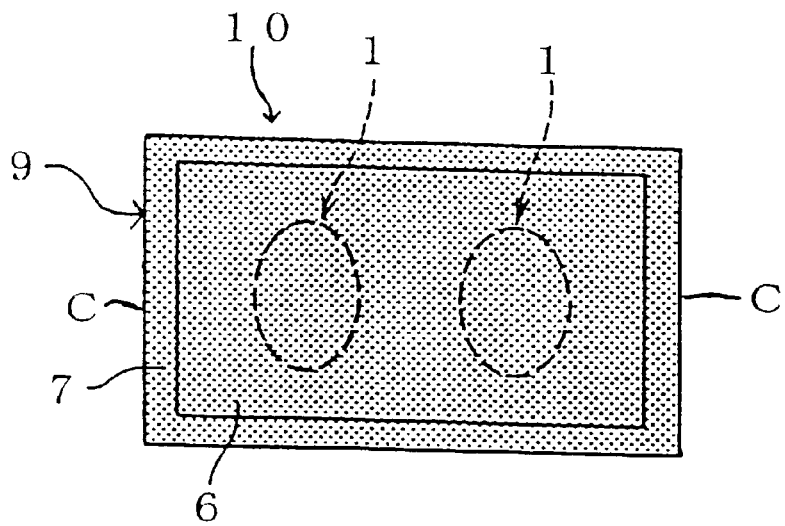
FIG. 3 shows another embodiment of the package of sheet-type patches of the invention.
Figure 3:
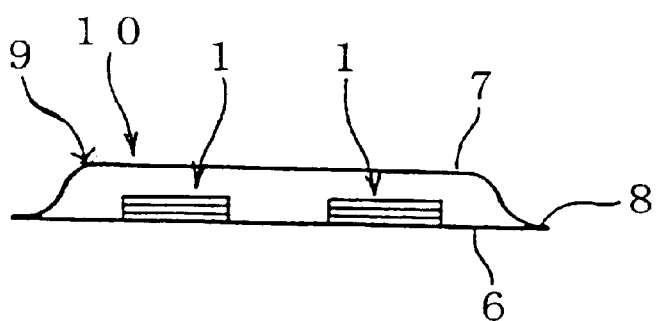
Figure 3:
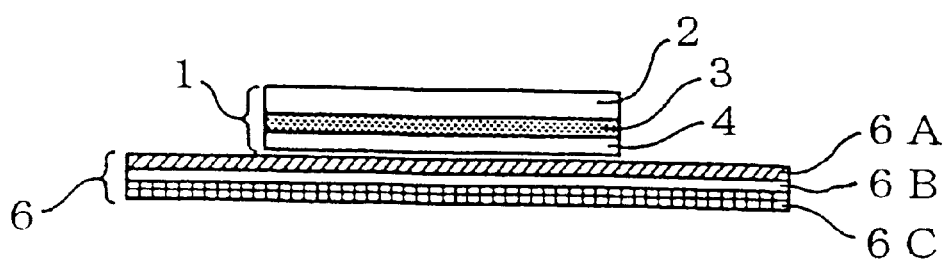
Figure 4:
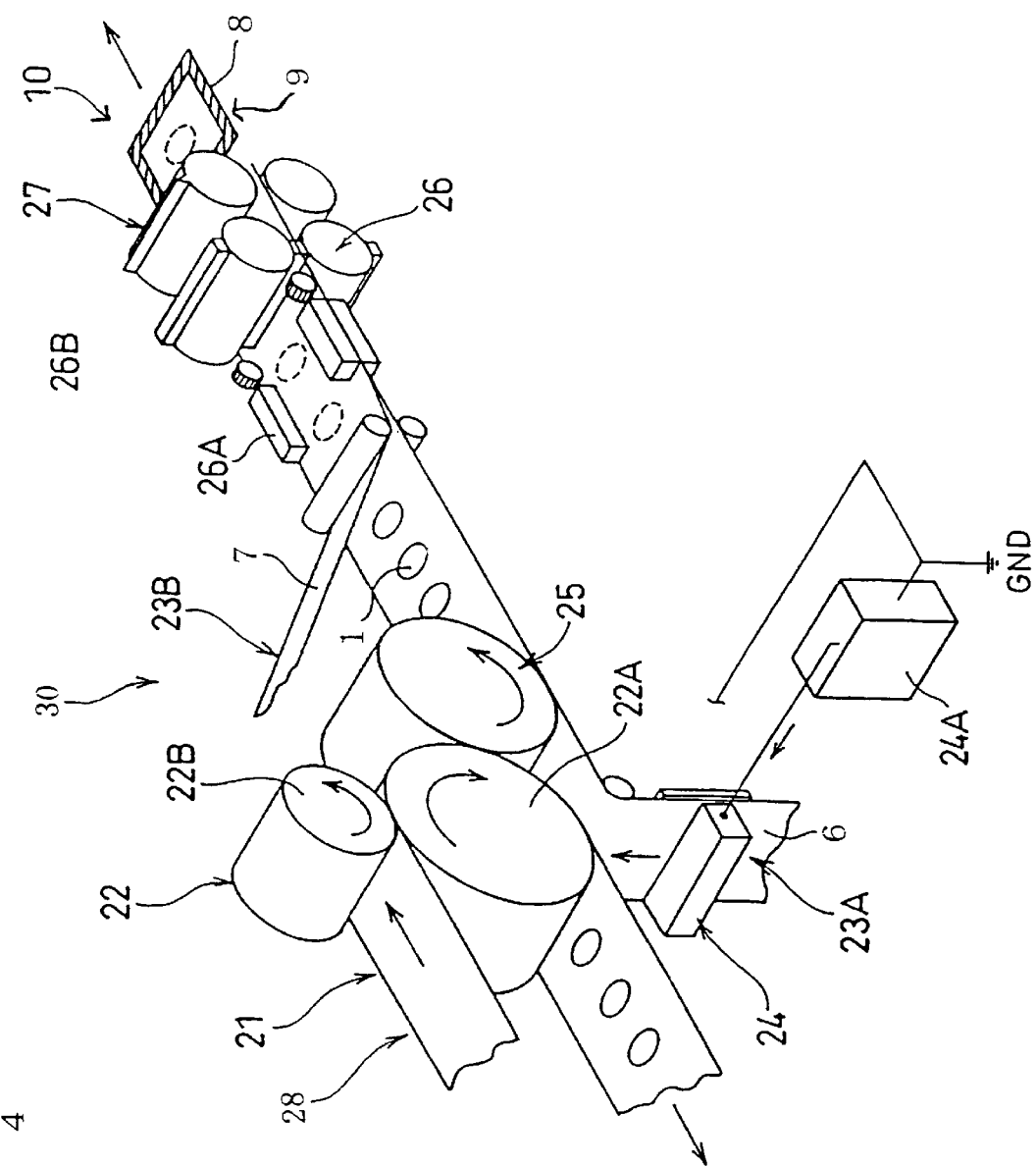
FIG. 4 is a graphical view showing one example of an apparatus for producing packages of sheet-type patches.

FIG. 3 shows another embodiment of the package of sheet-type patches of the invention; and FIG. 4 shows an apparatus for producing the package.

In this embodiment, a plastic laminate film is used as the packaging film 6 to form the package pouch 9. As the packaging film 6, for example, used is a multi-layered laminate film, which is composed of a heat-sealable, dielectric inner layer 6A of polypropylene (PP), a gas-barrier interlayer 6B of Al, and a protective outer layer 6C of PET for protecting Al. In this, the liner layer 4 of the patch 1 is preferably an easily chargeable synthetic resin of PET, PP, polyethylene or the like.

In this embodiment, at least one of the liner layer 4 of the patch 1 and the inner layer 6A of the packaging film 6 is previously charged, and the patches 1 are fixed onto the packaging film 6 via the liner layer 4 by means of the electrostatic force as generated by the charging. Another packaging film 7 is laid over the patches 1 having been fixed onto the packaging film 6, and the peripheral edges of those films are heat-sealed to form the package pouch 9.

The packages 10 can be produced, for example, in a packaging apparatus 30 shown in FIG. 4. The apparatus 30 comprises a sheet feeding device 21 via which a long sheet 28 for patches 1 is continuously fed into the apparatus; a cutting device 22 (having an anvil roll 22A and a die cutter 22B) in which the long sheet 28 is cut into patches 1 having a desired shape; a packaging film feeding device 23A via which a packaging film 6 is continuously fed into the apparatus; an electrostatically charging device 24 (having an electrode 24A) in which the packaging film 6 is previously charged; a transfer roll 25 which receives the sheet-type patches 1 having been cut in the cutting device 22, and transfers them onto the charged, packaging film 6 at predetermined positions thereon; a packaging film feeding device 23B via which another packaging film 7 is fed into the apparatus; a heat-sealing device 26 (having a side sealer 26A and an end sealer 26B) in which the packaging film 7 is laid over the packaging film 6 having the patches I as electrostatically fixed thereon, and the two films are heat-sealed together at the peripheral edges to form the sealed part 8; and a cutting device 27 in which the sealed part 8 of the films 6 and 7 is cut at the center of the end-sealed part to produce packages 10.

Various types of charging devices are usable herein as the electrostatically charging device 24. In one type, a large number of needle-like electrodes are brush-wise or comb-wise disposed in the widthwise direction of the packaging film 6 in such a manner that they are not in contact with the film 6. In another type, a metal roll is kept in contact with the film 6 in such a manner that its axial direction is perpendicular to the running direction of the film 6, and the roll is rotated in accordance with the running motion of the film 6. In still another type, conductive wires or the like are so extended in the widthwise direction of the film 6 that they are kept in contact with the full width of the film 6.

The method for producing the packages 10 in the apparatus 30 is described hereinunder.

First, the long sheet 28 having been fed via the long sheet feeding device 21 is cut in the cutting device 22 into sheet-type patches 1 having a desired shape. The sheet-type patches 1 are then vacuum-wise attracted by the transfer roll 25 at the side of the non-woven fabric 2 of each patch 1.

Meanwhile, the packaging film 6 having been fed via the packaging film feeding device 23A is electrostatically charged in the charging device 24. In this step, preferably, the inner layer 6A of the film 6 is charged.

Next, the sheet-type patches 1 having been vacuum-wise attracted to the transfer roll 25 are fixed onto the charged film 6 at predetermined positions by means of the electrostatic force. In this step, the vacuum-suction mode of the transfer roll 25 is switched to a pressure emission mode, whereby the patches 1 are transferred onto the film 6. In that manner, the sheet-type patches 1 are fixed onto the inner layer 6A of the film 6 via the liner layer 4 of each patch 1 by means of the electrostatic force. The surface of the transfer roll is preferably made of a conductive metal or the like in order to facilitate the transfer of the patches 1 from the roll onto the film 6.

Next, the other packaging film 7 having been fed into the apparatus via the packaging film feeding device 23B is laid over the film 6 having the patches 1 fixed thereon, and the two films are heat-sealed in the heat-sealing device 26 at the outer peripheral part to form the sealed part 8. Subsequently, in the cutting device 27, the sealed part 8 is cut at the center of the end-sealed part to produce packages 10 of sheet-type patches.

EXAMPLE 3

FIG. 5 shows one preferred embodiment of the shape of the sheet-type patch to be packaged in the invention.

The sheet-type patch 1 has a horse-beanlike shape, as shown in FIG. 5, which is so formed that the height A falls between 50 and 80 mm, the width B in the center part falls between 20 and 30 mm, the depth C in the concave part falls between 5 and 10 mm, the width D of the concave part is 40 mm or longer; and the radius of curvature E at the center of the concave part falls between 25 and 30 mm.

As having the illustrated shape, the fittability of the patch 1 to the areas outside and under the eyes is improved. In addition, the patch may be applied not only to the areas outside and under the eyes but also to the areas around the nasolabial grooves.

EXAMPLE 4

FIG. 6 shows another preferred embodiment of the shape of the sheet-type patch to be packaged in the invention.

For this embodiment, a pair of nearly L-shaped sheet-type patches 1, which are for skin-care use for treating the areas outside and under the eyes and the areas around the nasolabial grooves, are fixed onto a packaging film in such a manner that they face to each other. Where the pair of such patches are positioned in the illustrated manner, the space for the patches may be reduced, and if desired, a plural number of such patches may be packaged in one package pouch.

INDUSTRIAL APPLICABILITY OF THE INVENTION

The present invention provides a package of sheet-type patches, and a method for producing the same. According to the invention, the production efficiency in producing and packaging sheet-type patches is improved. In addition, in producing the package of sheet-type patches of the invention, raw materials for the patches are prevented from being wasted. Moreover, the sheet-type patches in the packages of the invention are prevented from moving and from adhering to each other.

What is claimed is:

1. A package of sheet-type patches, said package comprising:
    two layers of packaging film are sealed to each other along outer edges thereof to form a package pouch;
    a plurality of sheet-type patches enclosed within said package pouch, each of said plurality of sheet-type patches including:
        a substrate made of a non-woven fabric material;
        a pack agent layer formed on said substrate;
        a liner layer cover said pack-agent layer, wherein each of said plurality of sheet-type patches are fixed onto an inner surface of said package pouch via said liner layer.

2. The package of sheet-type patches according to claim 1, wherein each of said plurality of sheet-type patches are fixed onto said inner surface of said package pouch with an adhesive.

3. The package of sheet-type patches according to claim 1, wherein each of said plurality of sheet-type patches are fixed onto said inner surface of said package pouch by means of electrostatic force.

4. A method for producing packages of sheet-type patches, said method comprising the steps of:
    preparing a plurality of sheet-type patches by:
        forming a pack agent layer on a substrate, said substrate being made of a non-woven fabric material;
        covering said pack agent layer with a liner layer; and
        cutting said substrate, which has said pack agent layer and said liner layer thereon, into said plurality of sheet-type patches each having a desired shape;
    fixing each of said plurality of sheet-type patches onto an inner surface of a first layer of two layers of packaging film via said liner layer and an adhesive; and
    sealing together outer edges of said two layers of said packaging film to produce a package pouch enclosing said plurality of sheet-type patches.

5. A method for producing packages of sheet-type patches, said method comprising the steps of:
    forming a pack agent layer on a substrate, wherein said substrate is made from a non-woven fabric material;
    covering said pack agent layer with at least one liner layer;
    cutting said substrate, which has said pack agent layer and said at least one liner layer thereon, into a plurality of sheet-type patches each having a desired shape;
    electrostatically charging said at least one liner layer of each of said plurality of sheet-type patches and a first layer of two layers of packaging film;
    fixing each of said plurality of sheet-type patches onto said first layer of said two layers of packaging film via an electrostatic force; and
    sealing said two layers of said packaging film to each other at outer edges thereof to produce a package pouch enclosing said plurality of sheet-type patches.

* * * * *